United States Patent
Kanno et al.

(10) Patent No.: US 6,988,004 B2
(45) Date of Patent: Jan. 17, 2006

(54) METHOD FOR INDUCING ANGIOGENESIS BY ELECTRICAL STIMULATION OF MUSCLES

(75) Inventors: Shinichi Kanno, Pittsburgh, PA (US); Yasufumi Sato, Sendai (JP)

(73) Assignee: Bioheart, Inc., Sunrise, FL (US)

( * ) Notice: Subject to any disclaimer, the term of this patent is extended or adjusted under 35 U.S.C. 154(b) by 465 days.

(21) Appl. No.: 09/858,036

(22) Filed: May 15, 2001

(65) Prior Publication Data

US 2002/0031827 A1    Mar. 14, 2002

Related U.S. Application Data

(60) Provisional application No. 60/204,376, filed on May 16, 2000.

(51) Int. Cl.
*A61N 1/18* (2006.01)

(52) U.S. Cl. .............................. 607/50; 607/2

(58) Field of Classification Search ........... 607/1–2, 607/50; 128/897–898; 604/20–21
See application file for complete search history.

(56) References Cited

U.S. PATENT DOCUMENTS

| | | | | |
|---|---|---|---|---|
| 5,433,735 | A * | 7/1995 | Zanakis et al. | 607/50 |
| 6,240,314 | B1 * | 5/2001 | Plicchi et al. | 607/14 |
| 6,292,693 | B1 * | 9/2001 | Darvish et al. | 607/9 |
| 6,317,631 | B1 * | 11/2001 | Ben-Haim et al. | 607/9 |
| 6,330,476 | B1 * | 12/2001 | Ben-Haim et al. | 607/9 |
| 6,463,323 | B1 * | 10/2002 | Conrad-Vlasak et al. | 607/2 |
| 6,493,585 | B2 * | 12/2002 | Plicchi et al. | 607/14 |
| 6,810,286 | B2 * | 10/2004 | Donovan et al. | 607/2 |
| 2002/0010492 | A1 * | 1/2002 | Donovan et al. | 607/2 |

OTHER PUBLICATIONS

Hang, J., Kong L., Gu L., Adir TH. VEGF Gene Expression is Upregulated in Electrically Stimulated Rat Skeletal Muscle, *Am J. Physiol.* 1995;269:H1827-H1831.

Annex BH, Torgan CE, Lin P., Taylor DA, Thompson MA, Peters KG, Kraus WE. Introduction and Maintenance of Increased VEGF Protein by Chronic Motor Nerve Stimulation in Skeletal Muscle. *Am J. Physiol.* 1998;274:H860-H867.

Brown MD, Cotter MA, Hudlicka O., Vrbova G., The Effect of Different Patterns of Muscle Activity on Capillary Density, Mechanical Properties and Structure of Slow and Fast Rabbit Muscles. *Pflugers Arch.* 1976;361:241-250.

Hudlicka O., Tyler KR. The Effect of Long-Term High-Frequency Stimulation on Capillary Density and Fibre Types in Rabbit Fast Muscles. *J. Physiol.* 1984;353:435-445.

(Continued)

Primary Examiner—Kennedy Schaetzle
Assistant Examiner—Kristen Mullen
(74) Attorney, Agent, or Firm—Hodgson Russ LLP (57) ABSTRACT

The present invention comprises a method for stimulating angiogenesis. The method comprises the steps of electrically stimulating muscle below the threshold for muscle contraction.

5 Claims, 8 Drawing Sheets

OTHER PUBLICATIONS

Hudlicka O., Fronek K. The Effect of Long-Term Electrical Stimulation of Rabbit Fast Muscles on the Reactivity of Their Supplying Arteries. *J. Vasc Res*. 1992;29:13-19.

Mathieu-Costello O., Agey PJ, Wu L., Hang J., Adair TH. Capillary-to-Fiber Surface Ratio in Rat Fast-Twitch Hindlimb Muscles After Chronic Electrical Stimulation. *J. Appl Physiol*. 1996;80:904-909.

Hudlicka O., Price S. The Role of Blood Flow and/or Muscle Hypoxia in Capillary Growth in Chronically Stimulated Fast Muscles. *Pflugers Arch*. 1990;417:67-72.

Hudlicka O., Brown MD, Egginton S., Dawson JM. Effect of Long-Term Electrical Stimulation on Vascular Supply and Fatigue in Chronically Ischemic Muscles. *J Appl Physiol*. 1994;77:1317-1324.

\* cited by examiner

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: RT-PCR sense primer for Flk-1

<400> SEQUENCE: 1
aggggaactg aagacaggct a                                              21

<210> SEQ ID NO 2
<211> LENGTH: 21
<212> TYPE: DNA
<213> ORGANISM: Artificial Sequence
<220> FEATURE:
<223> OTHER INFORMATION: RT-PCR antisense primer for Flk-1

<400> SEQUENCE: 2
gatgctccaa ggtcaggaag t                                              21

<210> SEQ ID NO 3
<211> LENGTH: 20
<212> TYPE: DNA
<213> ORGANISM: Artificial Sequence
<220> FEATURE:
<223> OTHER INFORMATION: RT-PCR sense primer for VEGF

<400> SEQUENCE: 3
gtgcactgga ccctggcttt                                                20

<210> SEQ ID NO 4
<211> LENGTH: 20
<212> TYPE: DNA
<213> ORGANISM: Artificial Sequence
<220> FEATURE:
<223> OTHER INFORMATION: RT-PCR antisense primer for VEGF

<400> SEQUENCE: 4
aagctgcctc gccttgcaac                                                20
```

METHOD FOR INDUCING ANGIOGENESIS BY ELECTRICAL STIMULATION OF MUSCLES

This application claims priority to U.S. provisional application Ser. No. 60/204,376 filed on May 16, 2000, the disclosure of which is incorporated herein by reference.

FIELD OF INVENTION

The present invention relates generally to the field of angiogenesis. More particularly, the present invention provides a method for inducing angiogenesis by electrical stimulation.

DISCUSSION OF RELATED ART

Arterial occlusive diseases cause serious ischemia in various organs, such as the heart, brain, and leg. Therapeutic angiogenesis is thought to be beneficial for such conditions (Pepper, 1997, *Arterioscler Thromb Vasc Biol.*, 17:605–619). Local administration of recombinant angiogenic growth factors, such as basic fibroblast growth factor (bFGF) and vascular endothelial growth factor (VEGF), salvaged ischemic areas of myocardium and hindlimb in animal models (Baffour et al., 1992, *J. Vasc Surg.*, 16:181–191; Takeshita et al., 1994, *J Clin Invest.*, 93:662–670; Hariwala et al., 1996, *J Surg Res.*, 63:77–82; Banai et al., 1994, *Circulation.* 89:2183–2189; Yanagisawa-Miwa, 1992, *Science*, 257:1401–1403). However, the clinical application requires large amounts of these recombinant proteins and is not feasible at this time. Instead of recombinant proteins, use of gene therapy, i.e., in vivo transfection of angiogenic growth factor genes, has been attempted to treat these diseases. In particular, the clinical trial of intramuscular gene transfer of naked plasmid DNA encoding human $VEGF_{165}$ is progressing in the United States for the treatment of ischemic limbs (Baumgartner et al. *Circulation*, 1998, 97:1114–1123).

VEGF, a dimeric endothelial cell (EC)-specific growth factor, is thought to be a principal angiogenic factor that stimulates migration, proliferation, and expression of various genes in endothelial cells (ECs; Leung et al., 1989, *Science*, 246:1306–1309; Plate et al., 1992, *Nature*, 359: 845–848; Ferrara et al., 1992, *Endocrinol Rev.*, 13:18–32). VEGF is synthesized by cells around vasculature and affects ECs as a paracrine factor. The expression of VEGF is upregulated by hypoxia and various cytokines.

Although some of the factors involved in angiogenesis have been identified, no simple and practical method of therapeutic angiogenesis has heretofore been disclosed. Thus, there is an ongoing need to develop novel therapeutic approaches for inducing angiogenesis.

SUMMARY OF THE INVENTION

The present invention provides a method for inducing angiogenesis. The method comprises the steps of stimulating muscles by electrical stimulation at voltages and frequencies that do not cause their contraction. Using the method of the present invention, angiogenesis as well as an increase in VEGF expression was observed.

In one embodiment, when cultured skeletal muscle cells were electrically stimulated at a voltage and frequency that did not cause their contraction, vascular endothelial growth factor (VEGF) mRNA was augmented at an optimal-frequency stimulation. This increase of VEGF mRNA was derived primarily from transcriptional activation. Electrical stimulation increased the secretion of VEGF protein into the medium. This conditioned medium could augment the growth of endothelial cells. The effect of electrical stimulation was further confirmed in a rat model of hindlimb ischemia. The tibialis anterior muscle in the ischemic limb was electrically stimulated. The frequency of stimulation was 50 Hz and strength was 0.1 V, which was below the threshold for muscle contraction. Following a 5-day stimulation, there was a significant increase in blood flow within the muscle. Immunohistochemical analysis revealed that VEGF protein was synthesized and capillary density was significantly increased in the stimulated muscle. Rats tolerated this procedure very well, and there was no muscle contraction, muscle injury, or restriction in movement.

Accordingly, an object of the present invention is to provide a method for upregulating the VEGF in muscles by electrical stimulation.

Another object of the present invention is to provide a method for inducing angiogenesis by electrical stimulation.

BRIEF DESCRIPTION OF THE DRAWINGS

FIG. 2 is a representation of the analysis of stability of VEGF mRNA in C2C12 cells. Total RNA was extracted at indicated time points. Northern blotting and quantification of VEGF mRNA was performed. Percent remaining RNA was plotted as a function of time for electrical stimulation alone (○); actinomycin D without electrical stimulation (●); and actinomycin D with electrical stimulation (□).

FIG. 4A represents rat aortic smooth muscle cells (solid columns) and C2C12 cells (open columns) exposed to indicated frequencies for 24 hours. In FIG. 4B, C2C12 cells were electrically stimulated and conditioned medium was collected at indicated time points (solid columns) or C2C12 cells without electrical stimulation (open column). In FIG. 4C, conditioned medium of C2C12 cells with or without electrical stimulation was collected and the effect on cell number determined on BCECs.

FIG. 5 is a representation of the blood flow in rat tibialis anterior (TA) muscles on 7 and 14 days post operation. Electrical stimulation was continued from postoperative day 8 to day 12. Values are expressed as a percentage of blood flow in experimental muscles versus contralateral muscles. At postoperative day 7, blood flow in femoral artery (FA) excision alone (□) and FA excision with electrical stimulation (○) were significantly lower than in sham-operated limbs (Δ) (*P<0.01). At postoperative day 14, values in electrically stimulated in sham-operated limbs were significantly higher than those in FA excision alone (**P<0,01), and there was no significant difference in blood flow between stimulated and sham-operated limbs. All values are given as mean±SD.

DETAILED DESCRIPTION OF THE INVENTION

The present invention provides a simple and practical method for angiogenesis. The method of the present invention comprises the step of electrically stimulating the muscle at low voltage.

The term "low voltage" as used herein means, voltage that does not result in contraction of the muscle.

Electrical stimulation of cells may be carried out by standard techniques known in the art. For example, cells in culture may be electrically stimulated by immersing electrodes into the culture media and then passage of an electrical current. The electrodes need not touch the cells. For in vivo applications, electrodes may be implanted directly into the desired muscle. In the case of TA muscle, the electrodes may in implanted into the fascia of the TA muscle, tunneled subcutaneously and exteriorized at an appropriate location such as the scapulae and connected to a pulse generator. For application to the myocardium, electrodes may be applied via catheters or via implanted stimulators.

The electrical stimulation should be such that it does not induce contraction of the muscle. Although the electrical frequency and voltage useful for the method of the present invention varies with the cell type, it is preferable to use a frequency below 100 Hz. For the rat TA muscle, it was observed that 0.1V caused angiogenesis. This is about 10% of the threshold of muscle contraction. These values can easily be modified by those skilled in the art for therapeutic angiogenesis in individuals in need of treatment. An example of a useful frequency and voltage for smooth muscle is 25 Hz at 1V in vitro and for skeletal muscle is 50 Hz at 1.0V in vitro and 50 Hz at 0.1V in vivo.

The method of the present invention can be used to promote angiogenesis in damaged or ischemic muscle tissues. The muscles wherein angiogenesis can be stimulated include smooth, skeletal and cardiac.

The invention will be more clearly understood by the following examples which are intended to be illustrative and are not to be construed as restrictive.

EXAMPLE 1

This embodiment describes the induction of VEGF mRNA by electrical stimulation. To illustrate this embodiment, in vitro systems were used and VEGF, Flk-1 and GAPDH mRNA were evaluated. Flk-1 is a VEGF receptor and GAPDH was used as a housekeeping gene. Murine skeletal muscle cell line C2C12 cells were obtained from Riken Cell Bank; rat aortic smooth muscle cells from Hanno Research Center, Taiho Pharmaceutical Co Ltd; and human pulmonary artery smooth muscle cells from Kurabo. Cells were routinely cultured on plastic dishes in Dulbecco's Modified Eagle's Medium (DMEM, Nissui Pharmaceutical Co, Ltd) containing 10% fetal calf serum (FCS, Summit Biotechnology). Bovine capillary endothelial cells (BCECs) (obtained from Dr. T. Tamaoki, Kyowa Hakko Kogyo Co, Ltd) were grown in DMEM containing 10% FCS by standard methods such as described by Sato (1991, *Biochem Biophys Res Commun.*, 180:1098–1102). All primary cultures of passage <6 were used in following experiments.

Before conducting experiments on electrical stimulation, cells were preincubated for 24 hours in DMEM containing 0.1% BSA. Confluent cultures were electrically stimulated according to the method described by Brevet et al., (1976, *Science*, 193:1152–1154). Briefly, electrodes were immersed in the culture medium and electric current of 1.0V stimulus strength was passed at indicated frequencies (Hz) for the indicated time.

To analyze RNA, Northern blot analysis was carried out by standard methods such as described by Iwasaka et al. (1996, *J Cell Physiol.*, 169:522–531). Briefly, total RNA was extracted by the Acid Guanidium-Phenol-Chloroform method and fractionated on a 1% agarose gel containing 2.2 mol/L formaldehyde. The blots were then prepared by transfer onto a nylon filter (Hybond N+, Amersham). The filter was hybridized with a $^{32}$P-labeled probe in hybridization solution for 24 hours at 42° C. After the hybridization, the filter was washed in 2×SSC and 0.1% SDS at 60° C. and then in 0.2×SSC and 0.1% SDS at 60° C. Autoradiography was carried out on an imaging plate, and autoradiograms were analyzed with an image analyzer (FLA 2000 Fuji). The amount of VEGF mRNA was corrected for loading differences by the amount of ribosomal RNA. Human GAPDH cDNA templates were prepared by standard methods (Iwasaka et al., 1996, *J. Cell Physiol.*, 169:522–531). Flk-1 and VEGF cDNA templates were prepared by reverse-transcription polymearse chain reaction using the following primer pairs: Flk-1 sense (SEQ ID NO:1) and antisense (SEQ ID NO:2); VEGF sense (SEQ ID NO:3) and antisense (SEQ ID NO:4).

Figure 1A:
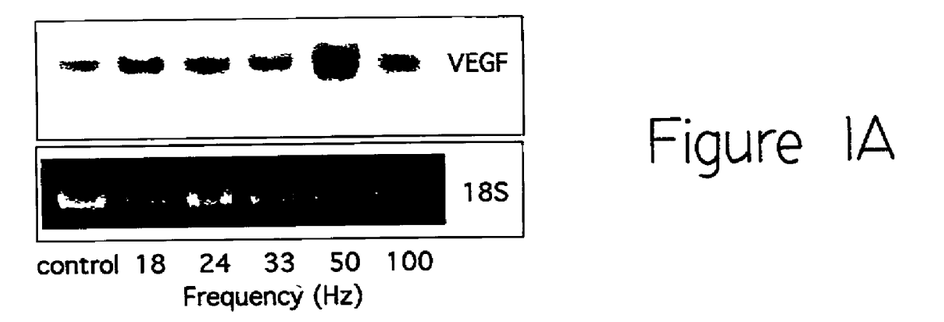
FIGS. 1A–C are representations of the expression of VEGF mRNA in cultured smooth muscle cells, skeletal muscle cells and flk-1 mRNA in BCECs. Cells were electrically stimulated for 24 hours at indicated frequencies, total RNA was extracted, and Northern blotting for VEGF mRNA or flk-1 mRNA was performed for murine skeletal muscle cell line, C2C12 cells (FIG. 1A), rat aortic smooth muscle cells (FIG. 1B), and BCECs (FIG. 1C).
Figure 1B:
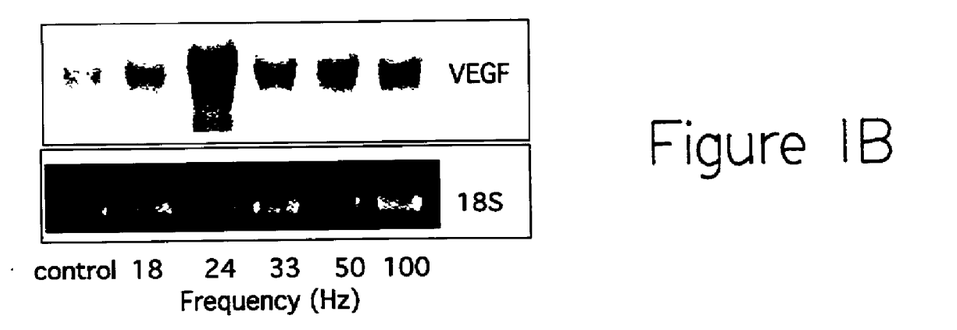
Figure 1C:
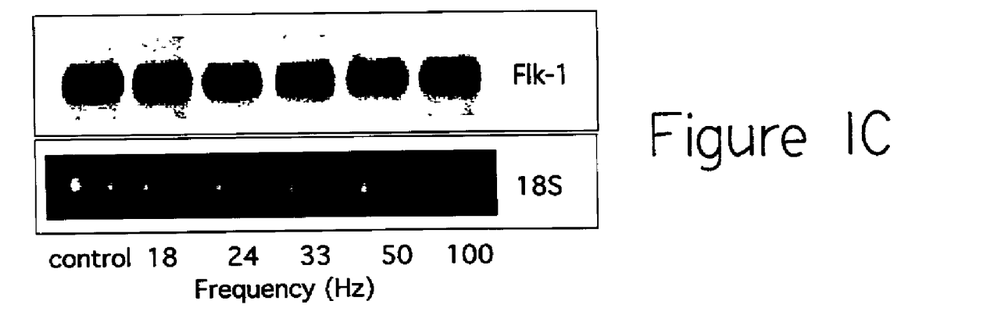

To determine whether electrical stimulation affects the expression of VEGF mRNA, cultured skeletal muscle cells were exposed to electrical pulse stimulation for 24 hours at various frequencies and 1.0 V strength, which did not cause their contraction or interfere with their spontaneous contraction. Northern blot analysis revealed that VEGF mRNA was augmented at specific frequencies. In murine skeletal muscle cell line C2C12 cells, the expression of VEGF mRNA was significantly augmented at the narrow range of frequencies around 50 Hz. (FIG. 1A). This frequency of electrical stimulation augmented the expression of VEGF mRNA in primary culture of rat skeletal muscle cells as well (data not shown). Although 50-Hz electrical stimulation seemed to be optimal for the expression of VEGF mRNA in skeletal muscle cells, it did not augment the expression of VEGF mRNA in rat aortic smooth muscle cells (FIG. 1B) or human fibroblasts (data not shown). Instead, the expression of VEGF mRNA was augmented at 24-Hz stimulation in rat aortic smooth muscle cells (FIG. 1B) as well as human pulmonary artery smooth muscle cells (data not shown). A time-course experiment revealed that VEGF mRNA was increased 4.8-fold in skeletal muscle cells and 4.5-fold in smooth muscle cells at the 8-hour time point at the proper frequency. To exclude the possibility that substances that might be released from the electrodes into the medium affected the expression of VEGF mRNA, the medium was electrically agitated and exposed to the cells. No augmentation of the expression of VEGF mRNA by this procedure was observed (data not shown). The expression of VEGF receptor-2 (KDR/Flk-1) mRNA in BCECs was not affected by electrical stimulation at various frequencies (FIG. 1C).

Figure 2:
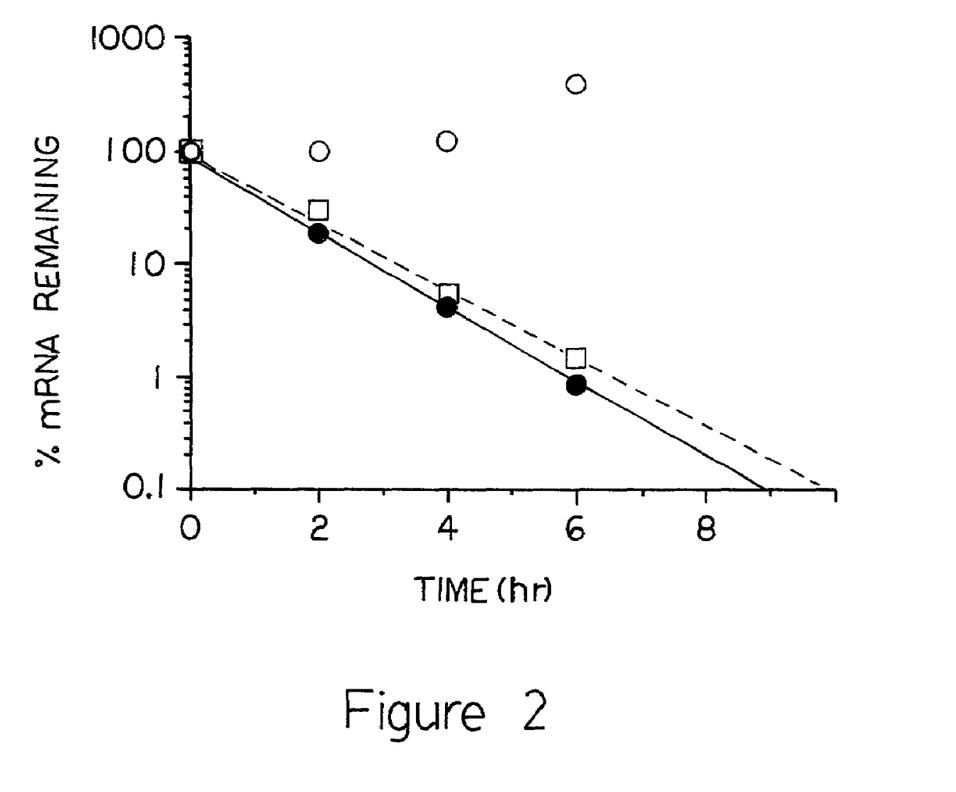

The level of expression of VEGF mRNA was determined by the transcription rate of VEGF gene and/or the stability of VEGF mRNA. An inhibitor of RNA synthesis, antinomycin-D (Act-D) was used to evaluate the stability of VEGF mRNA. Four µmol/L of Actinomycin D was added before electrical stimulation. Since Actinomycin D inhibits de-novo synthesis of mRNA the half-life of the previously synthesized mRNA could be studied. Total RNA was extracted at indicated time points and Northern blotting was performed. As shown in FIG. 2, the half-lives of VEGF mRNA, which were calculated by drawing the best-fit linear curve on a log-linear plot of the percentage of RNA remaining versus time in Act-D-treated cells, were 0.99 hour with electrically stimulation and 1.12 hour without electrical stimulation. Thus, electrical stimulation did not affect the stability of VEGF mRNA. Although not intending to be bound by any particular theory, these results suggest that the augmentation of VEGF mRNA by electrical stimulation was at the transcriptional level.

Figure 3:
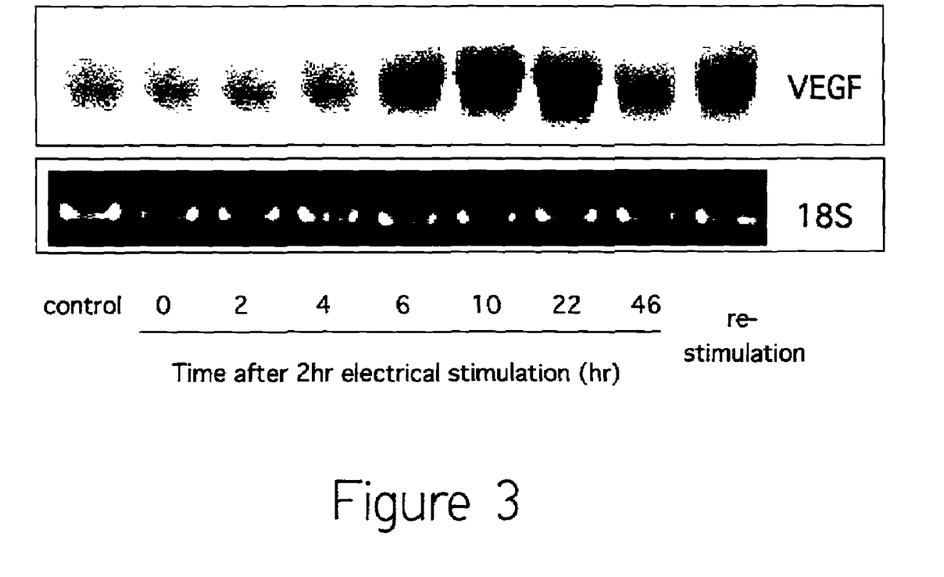
FIG. 3 is a representation of the time course of induction of VEGF mRNA by transient electrical stimulation. C2C12 cells were exposed to 2 hours of electrical stimulation and total RNA was extracted at indicated time points after transient electrical stimulation. "Control" indicates before stimulation, and "Restimulation" indicates that cells were stimulated a second time for 2 hours at 22 hours after first stimulation. Total RNA was extracted at 22 hours after second stimulation.

Next, the effect of transient electrical stimulation was examined. Cells were exposed to 2 hours of electrical stimulation, and then the total RNA was harvested at 22 hours after the transient stimulation. The results showed that the induction of VEGF mRNA was observed 22 hours after the transient-stimulation, and the level of its expression was almost identical to that of the continuous electrical stimulation for 24 hours (FIG. 3). Because VEGF mRNA returned to the basal level by 46 hours after a 2-hour electrical stimulation, the second stimulation could increase VEGF mRNA to a level comparable to the first stimulation. Thus, the transient electrical stimulation was equally effective and was repeatable.

EXAMPLE 2

This embodiment demonstrates that VEGF protein is synthesized and secreted into the medium upon electrical stimulation of the muscle according to the present invention. To illustrate this embodiment, C2C12 cells in DMEM containing 0.1% BSA were electrically stimulated for 24 hours at 1.0 V and 50 Hz, and the medium was collected. VEGF protein in the medium was measured by Quantikine-M ELISA kit (R&D Systems) according to the manufacturer's protocol.

Conditioned medium was collected from BCECs ($5\times10^4$) were plated on plastic dishes in DMEM with 10% FCS and incubated for 6 hours to allow attachment to the dish. The culture medium was replaced with either 100% conditioned medium, fresh medium (DMEM containing 0.1% BSA), or fresh medium supplemented with 10 ng/mL of recombinant human VEGF. Cell numbers were counted after 48 hours of incubation.

Figure 4A:
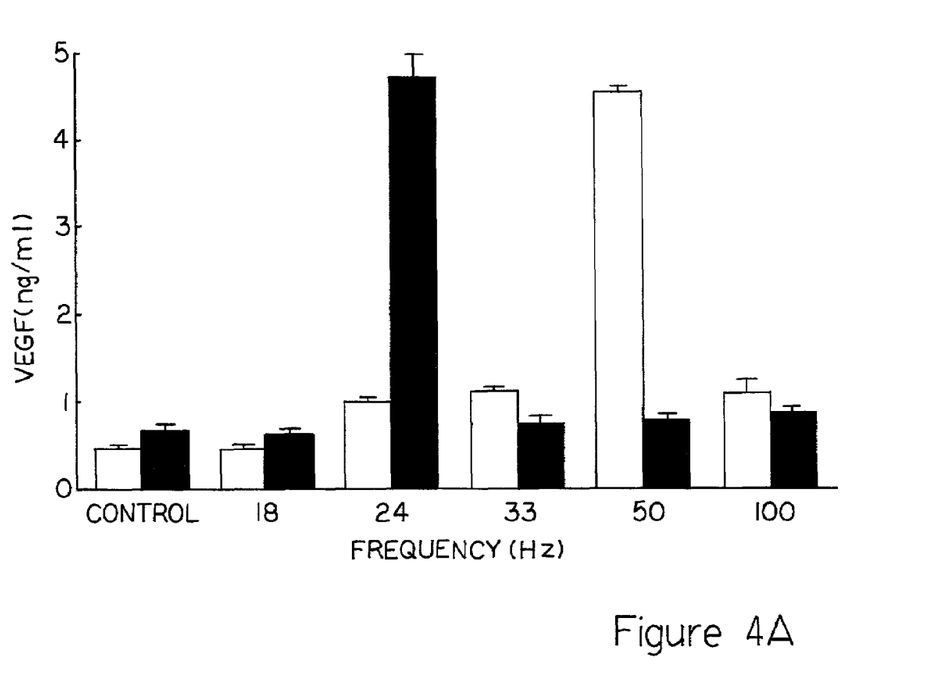
FIGS. 4A–4C is a representation of synthesis, secretion and biological activity of VEGF protein in conditioned medium collected during continuous electrical stimulation, and secreted VEGF protein in medium determined by ELISA.
Figure 4B:
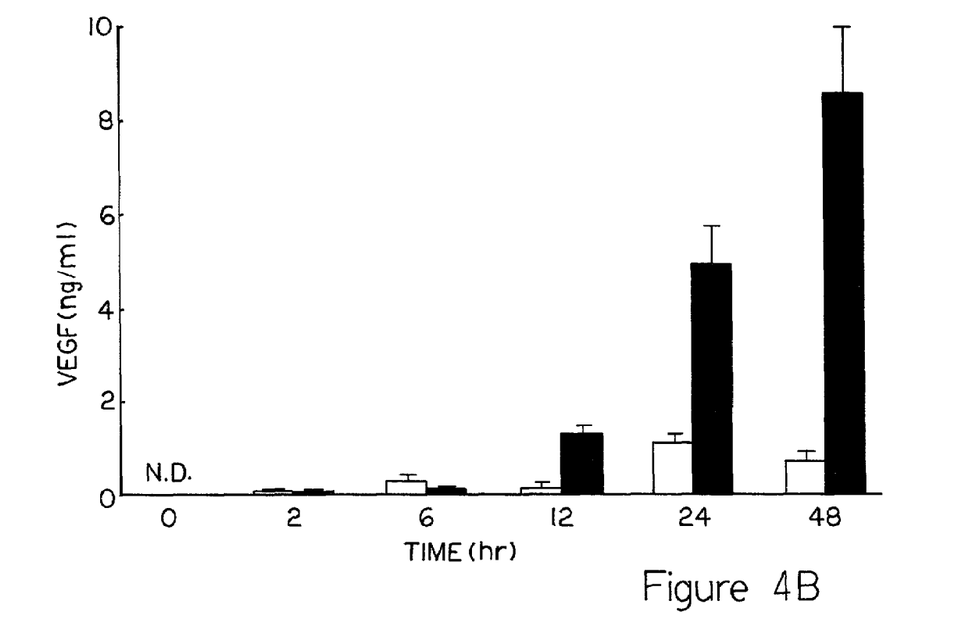
Figure 4C:
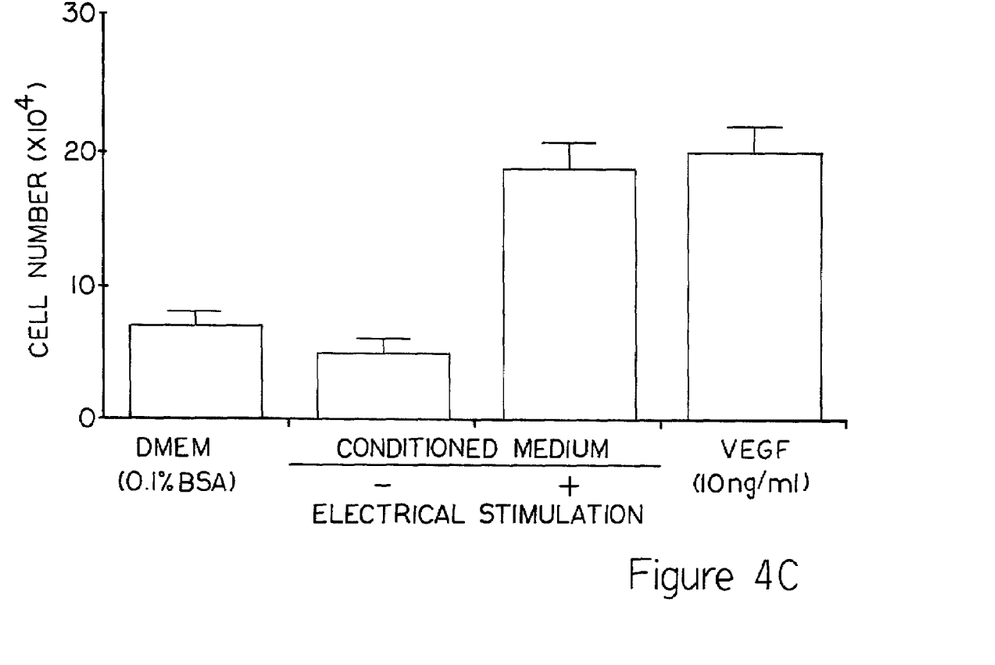

The synthesis and secretion of VEGF protein into the medium was analyzed by ELISA. VEGF in the medium of both C2C12 cells and rat aortic smooth muscle cells was increased by electrical stimulation (FIG. 4A). These stimulatory effects were observed to increase VEGF mRNA at the same specific frequencies in these cells. The elevation of VEGF protein in the medium was observed as early as 12 hours and reached its peak at 48 hours (FIG. 4B). The conditioned medium of electrical stimulation augmented the growth of BCECs as much as the medium supplemented with 10 ng/mL of human recombinant VEGF (FIG. 4C). Although proteins other than VEGF might also be responsible for the growth of BCECs, the concentration of VEGF in conditioned medium determined by ELISA suggested that most of the effects on the growth of BCECs were derived from VEGF and that electrical stimulation stimulated not only gene expression but also post transcriptional events in the synthesis of VEGF.

EXAMPLE 3

This embodiment demonstrates that electrical stimulation induces angiogenesis. This embodiment is illustrated by using a rat model of ischemic hindlimb. The parameters used to assess angiogenesis were immunohistochemical localization of VEGF, capillary density and blood flow. The statistical significance of differences in the results was evaluated by use of unpaired ANOVA, and a value of $P<0.05$ was accepted as statistically significant.

Male Sprague-Dawley rats (300 to 350 g body weight) were anesthetized with light ether sedation and subcutaneous injection of pentobarbital sodium (50 mg/kg) (Nembutal, Abbott Laboratories). The operation for hindlimb ischemia was performed according to the method described by Takeshita et al.(1996, *Lab Invest.,* 74:1061–1065). Briefly, the left femoral artery (FA) was completely excised from its proximal origin to the point distally at which bifurcates into the saphenous and popliteal arteries. After 1 week was allowed for recovery from the operation, blood flows of the bilateral tibialis anterior (TA) muscles were measured by the hydrogen gas clearance technique originally described by Aukland et al. (1964, *Circ Res.,* 14:164–187) and modified by Hori et al. (1996, *Int J Cancer.,* 65:360–364). Thereafter, the electrodes (Electrode for Functional Electrical Stimulation (FES), Nihonseisen) were implanted onto the facia of the left TA muscle, tunneled subcutaneously and exteriorized at the lever of the scapulae (Hang et al., 1995, *Am. J. Physiol.,* 269:H1827–H1831) and connected to a pulse generator (PulseCure, OG Giken). Electrical stimulation was started on the day after electrode implantation and continued for 5 days with a 0.3-ms stimulus width, 50-Hz stimulus frequency, and 0.1-V stimulus strength, which was far below the threshold of TA muscle contraction. The threshold of TA muscle contraction in this experimental condition detected by electromyogram was 1.1±0.2 V (data now shown). One day after the period of electrical stimulation, animals were anesthetized, blood flow was measured, and then the animals were killed for the procurement of bilateral TA muscles for further evaluations.

Animals were divided into 3 groups. In the first group (5 animals), TA muscles were continuously stimulated for 5 days after the dissection and excision of the left FA. In the second group (4 animals), electrodes were implanted after the dissection and excision of the left FA, but TA muscles were not electrically stimulated. The third group (6 animals) received a sham operation of the left FA and no electrical stimulation despite the implantation of electrodes. The contralateral hindlimb of each animal served as the control.

Figure 5:
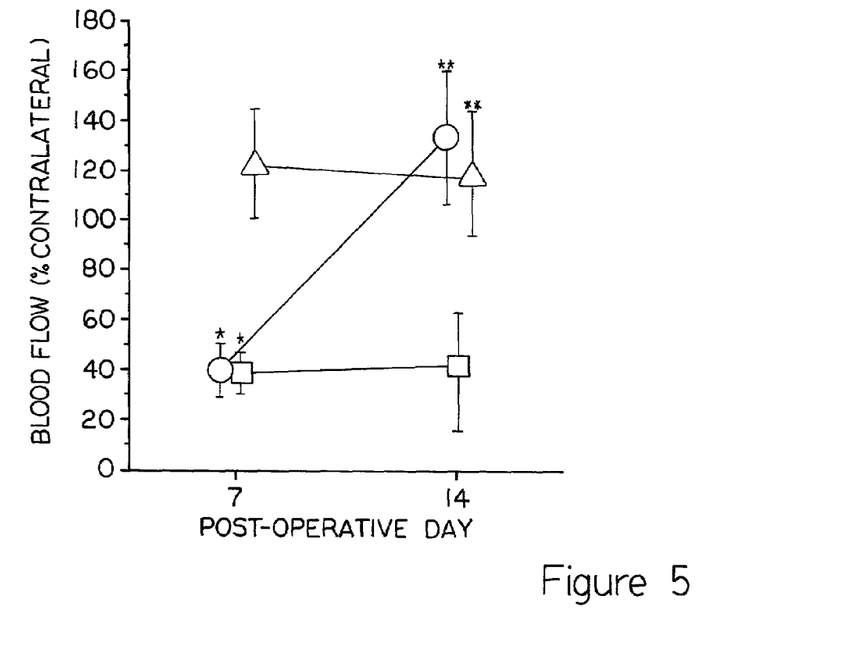

Blood flow was measured in TA muscles of ischemic and contralateral limbs. The percentage of blood flow in experimental muscles versus contralateral muscles is shown in FIG. 5. Blood flow in the ischemic limb (□) on day 7 after the left FA excision was significantly lower than that in the contralateral limb as well as in the sham-operated animals (Δ). Whereas blood flow in the ischemic limb on day 14 after the left FA excision did not increase without any stimulation (□), continuous electrical stimulation significantly increased blood flow in the TA muscle of the ischemic limb (○) In addition, rats tolerated this procedure very well, and there was no muscle contraction, muscle injury, or restriction in movement.

For detection of VEGF protein, muscle specimens were fixed with 10% formaldehyde, preincubated with 1% bovine serum albumin (BSA) for 30 minutes, and then incubated with rabbit polyclonal anti-VEGF antibody (1 µg/mL) (Santa Cruz Biotechnology) for 30 minutes at room temperature. Thereafter, the specimens were stained by the avidin-biotin complex method (Elite, Vector Laboratories, Inc.).

Figure 6:
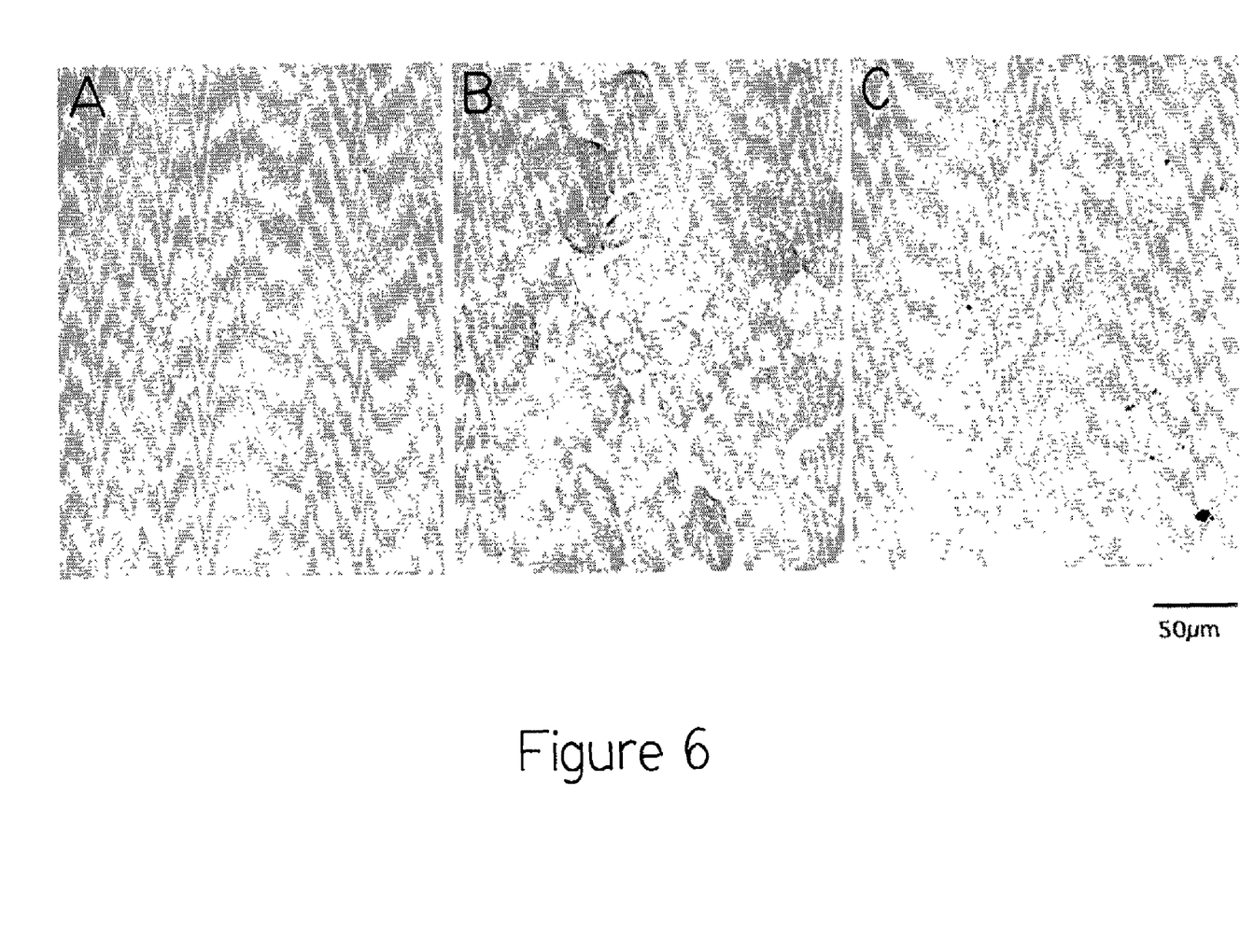
FIGS. 6A–C is a representation of immunohistochemical staining for VEGF protein in rat TA muscles for contralateral TA muscle (A), TA muscles after 5 days of electrical stimulation (B), and unstimulated TA muscle with FA excised (C).

As shown in FIGS. 6A–6C, immunostaining of TA muscles with polyclonal anti-VEGF antibody revealed a significant increase of VEGF protein in the muscle fibers of electrically stimulated TA muscles (6B) compared with unstimulated muscles (6C) or contralateral TA muscles (6C). This increase of VEGF protein was found only in the area between the electrodes on TA muscle.

Another parameter used to assess angiogenesis was capillary density. The number of capillaries and muscle fibers were counted in fixed sections of at least 8 different fields, and capillary density was obtained by the calculation of capillary number/fiber area.

Figure 7:
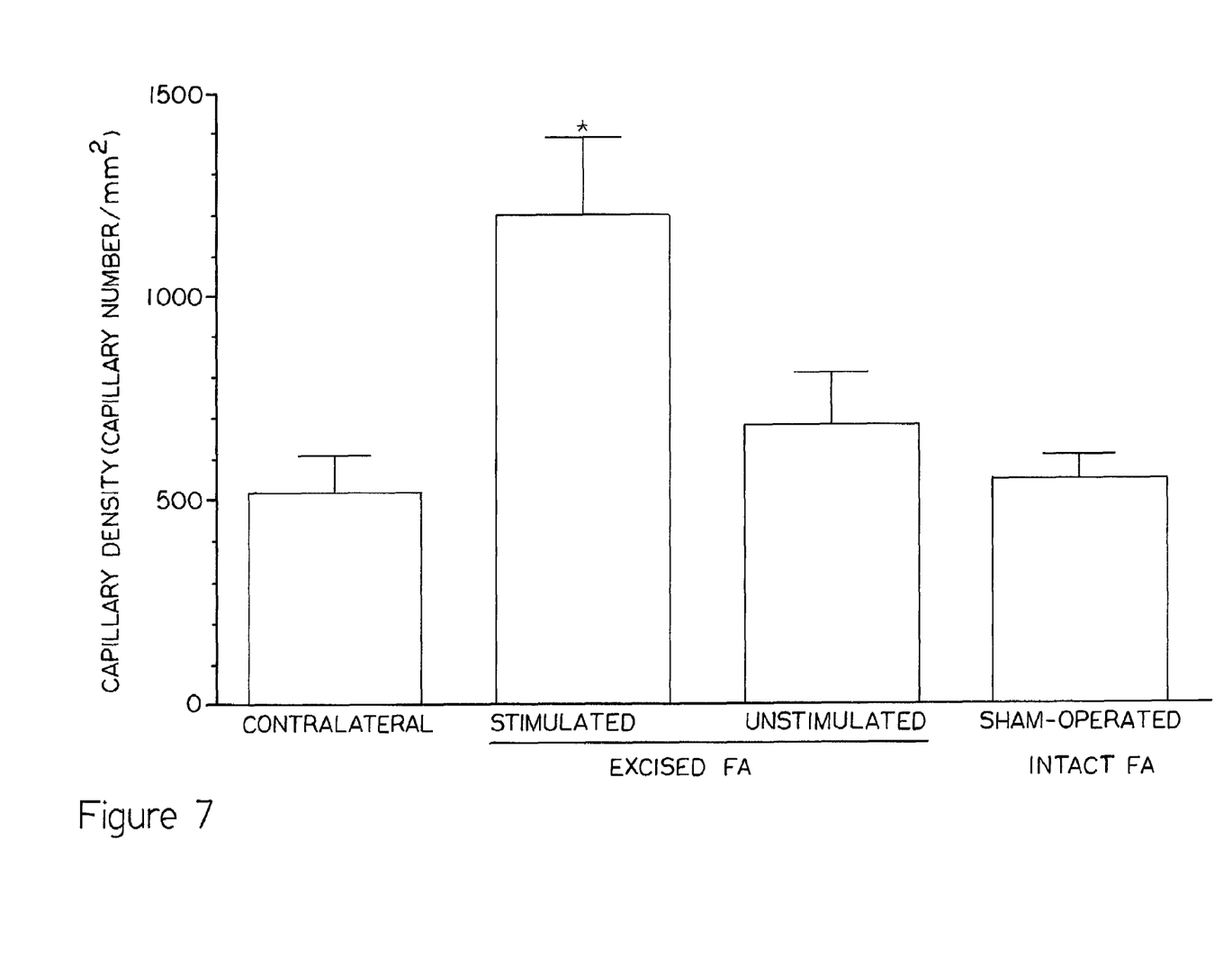
FIG. 7 is a representation of capillary density in rat TA muscles for contralateral, stimulated, unstimulated and sham-operated.
Figure 8A:
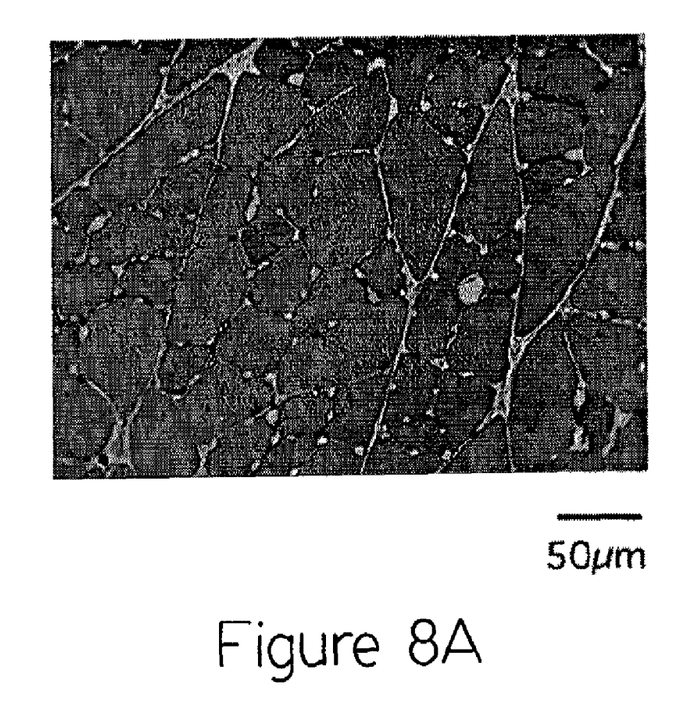
FIGS. 8A–8B is a representation of photomicrographs of muscles from lane 2 (FIG. 8A) and lane 3 (FIG. 8B) from FIG. 7.
Figure 8B:
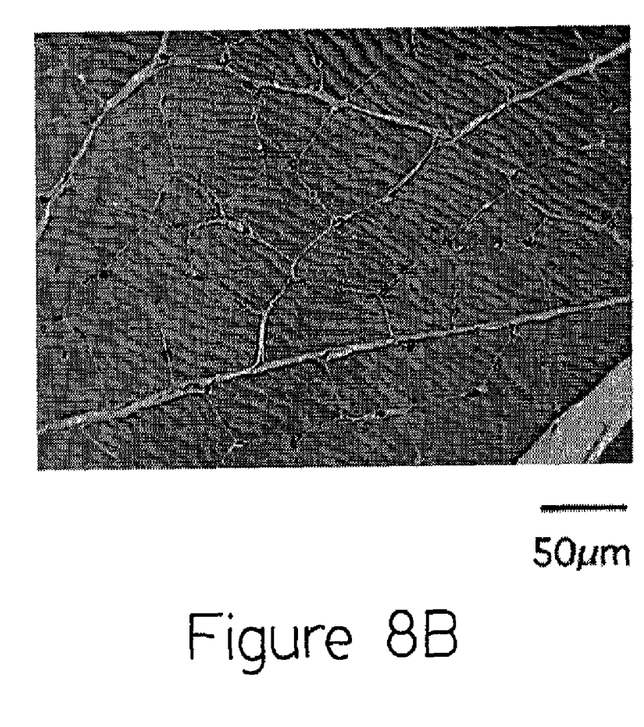

As shown in FIG. 7, capillary density of the stimulated muscles (lane 2) was increased ~2.5-fold compared with the contralateral muscles (lane 1) (P<0.01), whereas unstimulated animals (lane 3) as well as sham-operated animals (lane 4) had no significant difference between ischemic and contralateral muscles (FIG. 7). Representative images of the stimulated (A) and unstimulated (B) muscle from FIG. 7 are shown in FIG. 8, again demonstrating an increase in vasculature following electrical stimulation.

The data presented in this application demonstrates that electrical stimulation at low voltages that does not cause contraction, induces angiogenesis. While the invention has been described in detail, the above examples are illustrative and are not to be construed as restrictive. Various modifications of the present embodiments that are obvious to those skilled in the art are intended to be within the scope of the invention described herein.

What is claimed is:

1. A method for increasing VEGF mRNA in a muscle cell comprising the step of applying electrical voltage to the muscle cell, wherein the electrical voltage does not induce contraction of the muscle cell and wherein VEGF mRNA is increased after application of the electrical voltage.

2. The method of claim 1, wherein the voltage is 0.1V applied at a frequency of 50 Hz.

3. The method of claim 1, wherein the muscle is a smooth muscle.

4. The method of claim 1, wherein the muscle is a skeletal muscle.

5. The method of claim 1, wherein the muscle is a cardiac muscle.

* * * * *